US008475360B2

(12) United States Patent
Brown (10) Patent No.: US 8,475,360 B2
(45) Date of Patent: Jul. 2, 2013

(54) ENDOSCOPIC APPARATUS HAVING AN EXPANDABLE BALLOON DELIVERY SYSTEM

(75) Inventor: Hilbert D. Brown, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 1114 days.

(21) Appl. No.: 11/761,257

(22) Filed: Jun. 11, 2007

(65) Prior Publication Data

US 2007/0287885 A1    Dec. 13, 2007

Related U.S. Application Data

(60) Provisional application No. 60/812,659, filed on Jun. 9, 2006.

(51) Int. Cl.
*A61B 1/00*    (2006.01)
*A61B 1/04*    (2006.01)

(52) U.S. Cl.
USPC ........... 600/107; 600/123; 600/124; 600/125; 600/116

(58) Field of Classification Search
USPC .......... 600/107, 115, 116, 121–125; 604/160, 604/161, 164.05
See application file for complete search history.

(56) References Cited

U.S. PATENT DOCUMENTS

| 4,166,469 | A | * | 9/1979 | Littleford | 607/122 |
| 4,345,606 | A | * | 8/1982 | Littleford | 607/122 |
| RE31,855 | E | | 3/1985 | Osborne | |
| 4,581,025 | A | * | 4/1986 | Timmermans | 604/264 |
| 4,905,667 | A | | 3/1990 | Foerster et al. | |
| 5,167,239 | A | | 12/1992 | Cohen et al. | |
| 5,320,602 | A | * | 6/1994 | Karpiel | 604/514 |
| 6,309,379 | B1 | * | 10/2001 | Willard et al. | 600/467 |
| 6,419,624 | B1 | * | 7/2002 | Burton et al. | 600/29 |
| 6,770,066 | B1 | | 8/2004 | Weaver et al. | |
| 6,827,683 | B2 | | 12/2004 | Otawara | |
| 7,087,010 | B2 | * | 8/2006 | Ootawara et al. | 600/104 |
| 2005/0159645 | A1 | | 7/2005 | Bertolero et al. | |

FOREIGN PATENT DOCUMENTS

| JP | 07-096038 | 4/1995 |
| JP | 09-108356 | 4/1997 |
| WO | WO 01/47591 A1 | 7/2001 |
| WO | WO 2006/031596 A2 | 3/2006 |

OTHER PUBLICATIONS

International Search Report—PCT/US2007/070885 (Nov. 7, 2007).

* cited by examiner

*Primary Examiner* — Alireza Nia
(74) *Attorney, Agent, or Firm* — Brinks Hofer Gilson & Lione (57) ABSTRACT

An apparatus cooperable with a grasping slot of an elevator for an endoscope is disclosed. The apparatus comprises an expandable balloon disposable through the endoscope for dilitating a stricture in the body duct. The apparatus further comprises a catheter disposable about the expandable balloon and through the endoscope. The catheter comprises proximal and distal portions along a longitudinal axis thereof. At least the proximal portion comprises a splittable portion formed therealong to define first and second sections separable from each other for securing the catheter while protecting and maintaining the expandable balloon at the stricture.

16 Claims, 6 Drawing Sheets

ENDOSCOPIC APPARATUS HAVING AN EXPANDABLE BALLOON DELIVERY SYSTEM

CROSS-REFERENCE TO RELATED APPLICATIONS

This application claims the benefit of U.S. Provisional Application Ser. No. 60/812,659, filed on Jun. 9, 2006, entitled "ENDOSCOPIC APPARATUS HAVING AN EXPANDABLE BALLOON DELIVERY SYSTEM," the entire contents of which are incorporated herein by reference.

FIELD OF THE INVENTION

The present invention relates to medical devices, and more particularly, to endoscopic apparatus having balloon catheter delivery systems.

BACKGROUND OF THE INVENTION

Endoscopic devices have been commonly used for various procedures, typically in the abdominal area. Endoscopy is the examination and inspection of the interior of body organs, joints or cavities through an endoscope. Endoscopy allows physicians to peer through the body's passageways. An endoscopic procedure may be used to diagnose various conditions by close examination of internal organ and body structures and may also guide therapy and repair, such as the removal of torn cartilage from the bearing surfaces of a joint. A biopsy, a procedure involving tissue sampling for pathologic testing, may also be performed under endoscopic guidance. For example, endoscopic procedures include the following known procedures: gastroscopy, sigmoidoscopy and colonoscopy, esophago gastro duodenoscopy (EGD), endoscopic retrograde cholangiopancreatography (ERCP), and bronchoscopy.

The use of endoscopic treatments has recently increased for some diseases occurring in the gastrointestinal or pancreatobiliary duct systems. Endoscope systems are used frequently for diagnostic procedures, including contrast imaging of biliary or pancreatic ducts. Endoscopes are also used in procedures for retrieving gallstones that exist in the common bile duct and elsewhere.

Typically, these treatments are performed in the pancreatic duct, bile duct, and the hepatic duct by positioning the distal end of an endoscope in the vicinity of the duodenal papilla. Once the endoscope is in place, a wire guide is delivered to the target anatomy via the working channel of the endoscope. In order to guide the wire guide (or other medical instruments), out of the working channel of the endoscope, a rigid elevator is typically used to orient or deflect the distal end of the wire guide. When the distal end of the wire guide is properly oriented, the wire guide is inserted into the target anatomy.

At this point in the procedure, a catheter or similar treatment instrument can be passed over the wire guide either in a conventional over-the-wire style or in a rapid exchange style to the target anatomy. In order to limit movement of the wire guide relative to the target anatomy, the distal or proximal ends of the guide wire can be locked relative to the endoscope.

Many current endoscopic systems include endoscopes having an elevator used to orient the wire guide and to lock the distal end of the wire guide. In many of such endoscopes, the elevator includes a v-shaped groove. The v-shaped groove is typically used to guide the wire guide to a central position relative to the endoscope. The elevator having a v-shaped groove is further used to lock the distal end of the guide wire.

However, when an inflatable balloon is used, there is a risk that the balloon may get caught within the groove. This is undesirable. Moreover, clinicians have been challenged in accurately positioning the inflatable balloons during an endoscopic procedure.

Thus, there is a need for an endoscopic apparatus that protects an inflatable balloon and maintains it position to ensure accuracy when deploying an inflatable balloon to dilate a stricture.

BRIEF SUMMARY OF THE INVENTION

The embodiments of the present invention provide an endoscopic apparatus having an outer catheter that protects an expandable balloon for diliation of a stricture in a body duct. The catheter maintains its position at the stricture to ensure an accurate deployment of the expandable balloon.

In one embodiment, the present invention provides an endoscopic apparatus cooperable with an endoscope for treatment of a stricture in a body duct. The apparatus comprises an expandable balloon disposable through the endoscope for dilitating a stricture in the body duct. The apparatus further comprises a catheter disposable about the expandable balloon and through the endoscope. The catheter comprises proximal and distal portions along a longitudinal axis thereof. At least the proximal portion comprises a splittable portion formed therealong to define first and second sections separable from each other for securing the catheter while protecting and maintaining the expandable balloon at the stricture.

In another embodiment, the present invention provides an endoscopic system. The system comprises an insertion tube extending to a distal tip and includes an elevator movably attached thereto. The elevator has an inner side formed thereon defining a grasping slot. The system further comprises an expandable balloon disposable through the insertion tube for dilitating a stricture. The system further comprises a catheter through which the expandable balloon is disposed. The catheter is disposed through the insertion tube. The catheter is cooperable with the grasping slot to inhibit longitudinal movement of the catheter with respect to the elevator. The catheter comprises proximal and distal portions along a longitudinal axis thereof. At least the proximal portion comprising splittable portions formed along the longitudinal axis to define first and second sections separable from each other at the splittable portions for securing the catheter while protecting and maintaining the expandable balloon at the stricture.

In another example, a method of treating a stricture in a body duct with an endoscope comprising an insertion tube having a distal tip with an elevator. The method comprises introducing a catheter through the insertion tube adjacent to the elevator of the distal tip. The catheter has an expandable balloon disposed therein for delivery to the stricture for dilatation. The catheter comprises proximal and distal portions along a longitudinal axis thereof. At least the proximal portion comprises splittable portions formed along the longitudinal axis to define first and second sections separable from each other at the splittable portions. The method further comprises moving the elevator to position the catheter adjacent the stricture in the body duct and separating the first and second portions at the proximal portion of the catheter to longitudinally maintain the catheter relative to the balloon. The method further comprises deploying the balloon through the catheter in the body duct for treatment of the stricture.

Further objects, features, and advantages of the present invention will become apparent from consideration of the

DETAILED DESCRIPTION OF THE INVENTION

The present invention generally provides an endoscopic apparatus for treatment of a stricture in a body duct. Embodiments of the present invention comprise a catheter for delivery of a balloon through an endoscope to the stricture in the body duct. The catheter protects the balloon from the elevator of the endoscope. The catheter comprises splittable portions formed along the longitudinal axis to define first and second sections separable from each other at the splittable portion for securing the catheter while protecting and maintaining the inflatable balloon at the stricture.

Figure 1A:
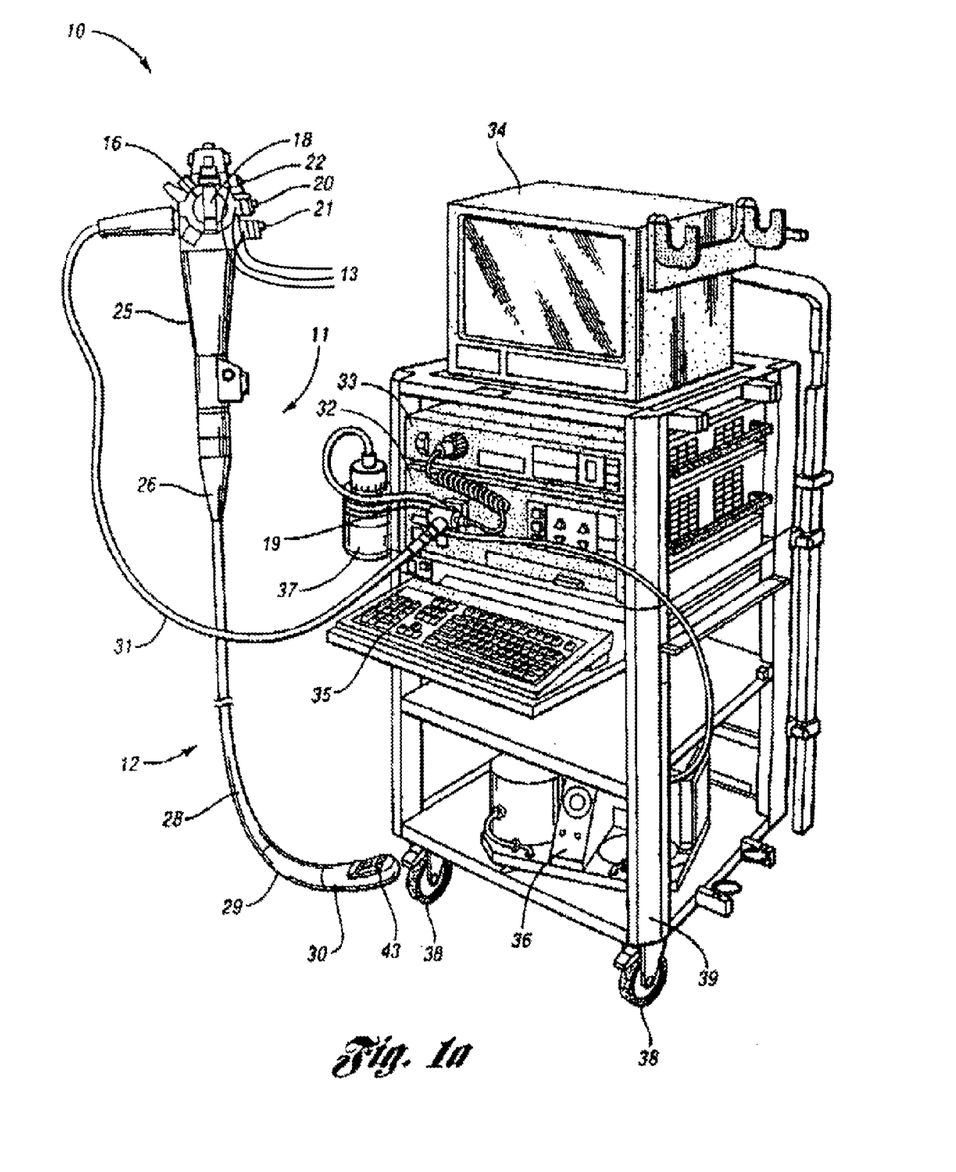
FIG. 1a is a perspective view of an endoscopic system comprising an endoscope in accordance with one embodiment of the present invention.
Figure 1B:
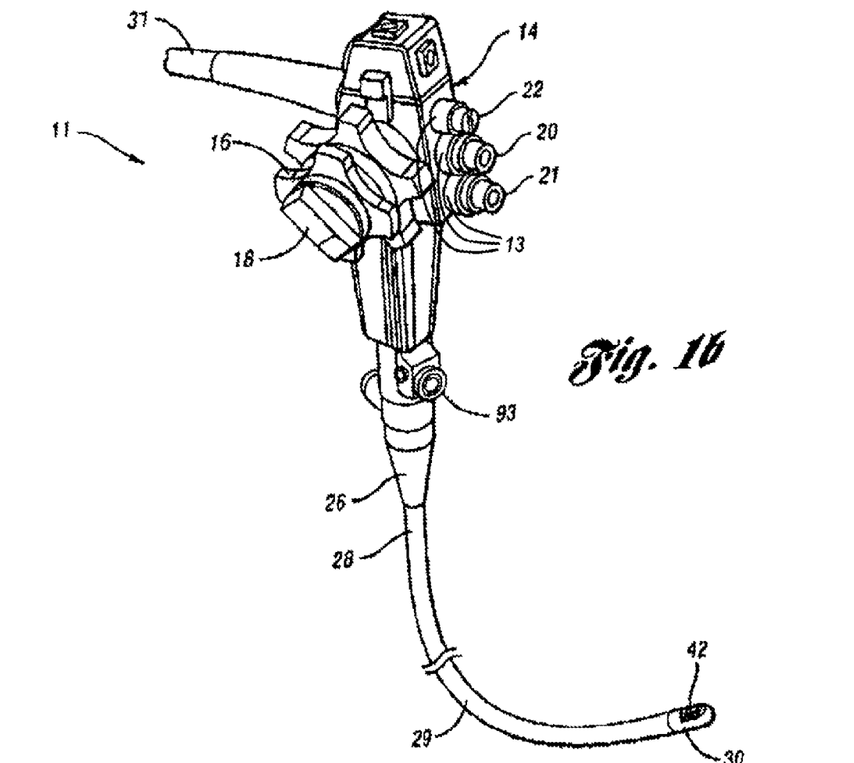
FIG. 1b is a perspective view of the endoscope depicted in FIG. 1A.
Figure 1C:
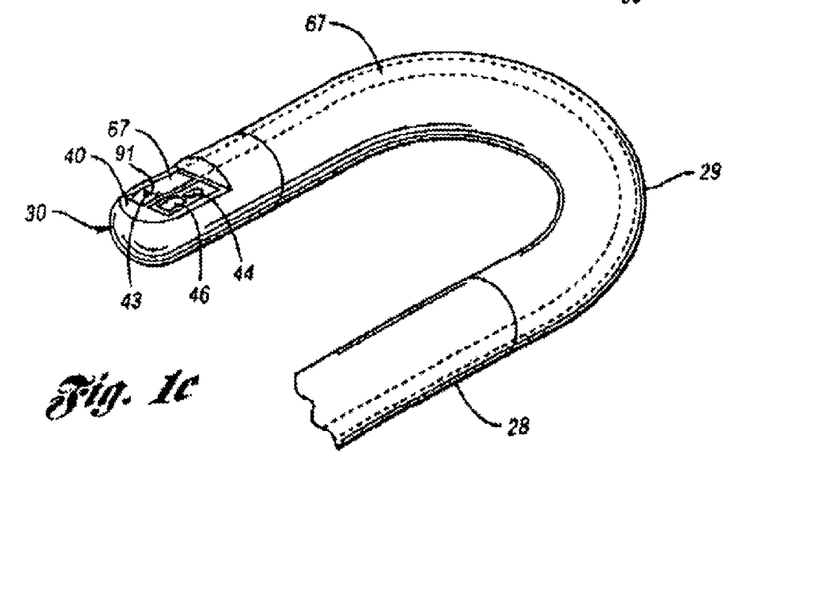
FIG. 1c is an elevated view of a distal tip of the endoscope in accordance with one embodiment of the present invention.
Figure 2:
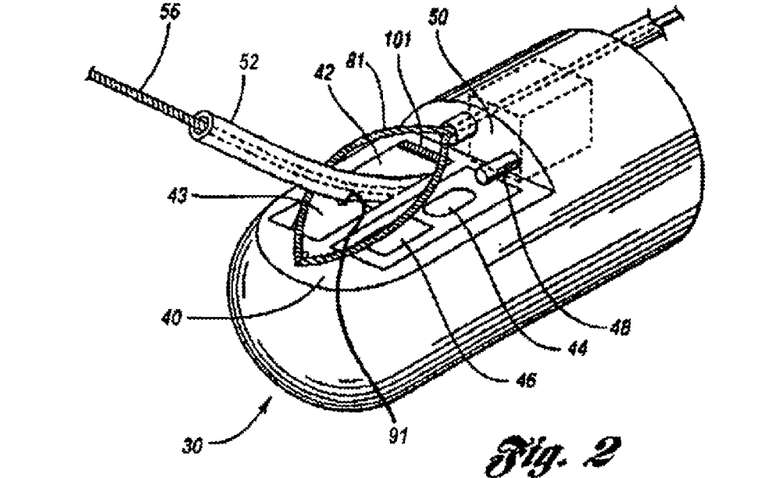
FIG. 2 is an enlarged view of the distal tip of the endoscope in accordance with one embodiment of the present invention.
Figure 3:
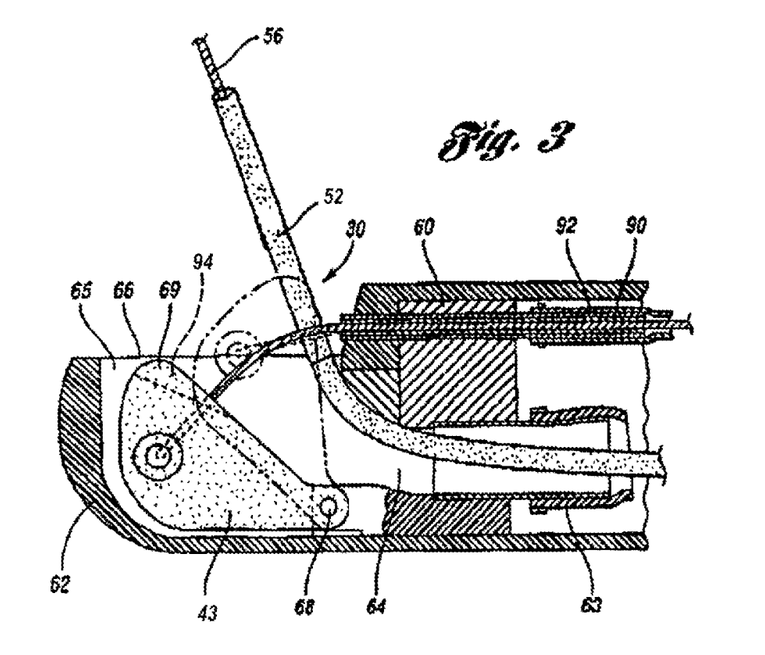
FIG. 3 is a cross-sectional view of the distal tip of the endoscope insertion portion of the endoscope taken along line 3-3.

FIGS. 1-3 illustrate an endoscopic system comprising an endoscope having an elevator with a distal tip. Additional details relating to the endoscopic system are described in U.S. Pat. No. 6,827,683, entitled "ENDOSCOPE SYSTEM AND MEDICAL TREATMENT METHOD" issued Dec. 7, 2004 to Takashi Otawara, which is incorporated herein by reference in its entirety.

FIG. 1a illustrates an endoscopic system 10 comprising an endoscope 11 in accordance with one embodiment of the present invention. In this embodiment, the endoscope 11 comprises an insertion tube 12 to be inserted into a body cavity for various endoscopic procedures including gastroscopy, sigmoidoscopy and colonoscopy, esophago gastro duodenoscopy (EGD), endoscopic retrograde cholangiopancreatography (ERCP), and bronchoscopy. As shown, the endoscope 11 comprises an insertion tube 12 having a plurality of channel ports 93 through which endoscopic units may be disposed. In one embodiment, endoscopic units disposed in one of the ports may include one embodiment of an improved elevator having a tip.

As shown in FIGS. 1a and 1b, the endoscope 11 further include a control system 14 that is in mechanical and fluid communication with the insertion tube 12. The control system 14 is configured to control the insertion tube 12 and endoscopic parts disposed therein. As shown, the control system 14 includes first and second control knobs 16, 18. The control knobs 16, 18 are configured to be in mechanical communication with the insertion tube 12. The control knobs 16, 18 allow the physician to control and guide, by known means, the insertion tube 12 through vessels and cavities of a patient. The control system 14 further includes valve switches (e.g., suction valve 20, air/water valve 21, camera valve 22), each of which are in communication to one of the channel ports 93 of the insertion tube 12. For example, the suction valve switch 20, when activated, allows a vacuum from a suction source through a suction channel port for suctioning unwanted plaque and debris from the patient. In one example, the distal end of the insertion tube 12 is inserted, rectally or orally, to a predetermined endoscopic location within a patient. Insertion of the insertion tube 12 may be rectally or orally depending on the endoscopic procedure.

In this embodiment, the insertion tube 12 comprises an operating portion 25 connected to the control system 14 and extending to an insertion portion protecting member 26. A control system 20 is connected to the operating portion 25 and is configured to control the insertion tube 12. In this embodiment, the insertion tube 12 is composed of components that include a flexible tube 28, a flexure 29 connected to the flexible tube 28, and an endoscope tip 30 connect to the flexure 29. A universal cord 31, on one end, is connected and in communication with the control system 20. On the other end, the cord 31 has a connector 19 attached thereto. The connector 19 is in communication to a light guide tube and electrical contact, and is connected to a light source apparatus 32 and an image processing apparatus 33 (external devices). These external devices may include a monitor 34, an input keyboard 35, a suction pump apparatus 36, and an irrigation bottle 37, and other suitable apparatus are installed on a rack 39 equipped with rollers 38.

As shown in FIGS. 1c and 2, a cutout 40 is formed on the outer circumferential surface of the tip 30. In this embodiment, a channel opening 42 is formed on one side of the cutout 40, and an objective lens 44 and a light source 46 are disposed on another side of the cutout 40 for imaging. Both the objective lens 44 and the light source 46 are positioned adjacent to the channel opening 42. The tip 30 further comprises a nozzle 48 extending from a back wall surface 50 of the cutout 40. The nozzle 48 allows a stream of water, air, or the like to be sprayed towards the outer surface of the objective lens 44 to clean the lens surface.

FIGS. 1c and 2 further illustrate the elevator 43 comprising a grasping slot 91 in accordance with one embodiment of the present invention. The grasping slot may take on any suitable shape or form for grasping of a medical device. In this embodiment, the grasping slot 91 is narrowly formed by inner sides 94 that define the grasping slot 91 formed through the elevator 43. Preferably, the grasping slot 91 is centrally formed through the elevator 43 for receiving a medical device (e.g., catheter or wire guide) and grasping the device during operation of the endoscope.

As depicted in FIG. 2, tip 30 further includes a guide catheter 52 and a wire guide 56 disposed through the guide catheter 52. The tip 30 further includes an elevator 43 configured to receive the guide catheter and/or wire guide for elevating the guide catheter 52 or wire guide 56. As will be described in greater detail below, the elevator 43 is comprised of polymeric material and has a grasping slot formed therethrough for enhanced grasping and reduced scraping purposes.

The elevator 43 is pivotally attached to the tip 30 and is configured to receive the medical instrument (e.g., catheter or wire guide) for elevating the medical instrument. As shown in FIG. 3, the distal tip houses the elevator 43 in channel opening 42. The elevator 43 is used to orient medical instruments such as a catheter. As discussed in greater detail below, this is accomplished by engaging the medical instrument and pivoting away from the distal tip thereby laterally moving the distal end of the medical instrument away from the distal tip. The elevator 43 thus secures the distal end of the medical instrument relative to the endoscope. That is, as the medical instrument is received in slot 91 of the elevator 43, the medical instrument laterally moves relative to the tip 30 when the elevator 43 pivots therefrom.

FIG. 3 illustrates that the endoscope tip 30 includes a cuff 60 as the main body of the tip 30, and a sleeve or cover 62 that covers the perimeter of the cuff 60. As shown, the cover 62 is formed using a nonconductive member such as any suitable polymeric material, e.g., high density polyethylene or polypropylene. In this embodiment, the cover 62 is attached to the cuff 60 by any suitable means, e.g., by adhesive bonding. The cuff 60 is disposed adjacent the working channel 63, which acts as a passageway for the insertion of the medical instrument, e.g., wire guide or catheter. In this embodiment, a channel 67 (FIG. 1c) is formed through the tip 30 such that the tip opening of the treatment instrument is able to be disposed through channel opening 42.

FIG. 3 further illustrates an elevator wire 90 connected to the elevator 43. In this embodiment, the elevator wire 90 is located at the operating portion 25 and extends through a guide tube 92 and a guide pipe 93 connected to the guide tube 92. The elevator wire 90 is in mechanical communication with the control system 14 so that manipulations at the control system 14 result in movement of the elevator wire 90 relative to the endoscope. FIG. 3 depicts (in phantom) movement of the elevator 43 when the elevator wire 90 is actuated at the control system 14, moving the position of the elevator 43 about the elevator turning support 68 as the elevator wire 90 is retracted or pulled.

Figures 4, 5:
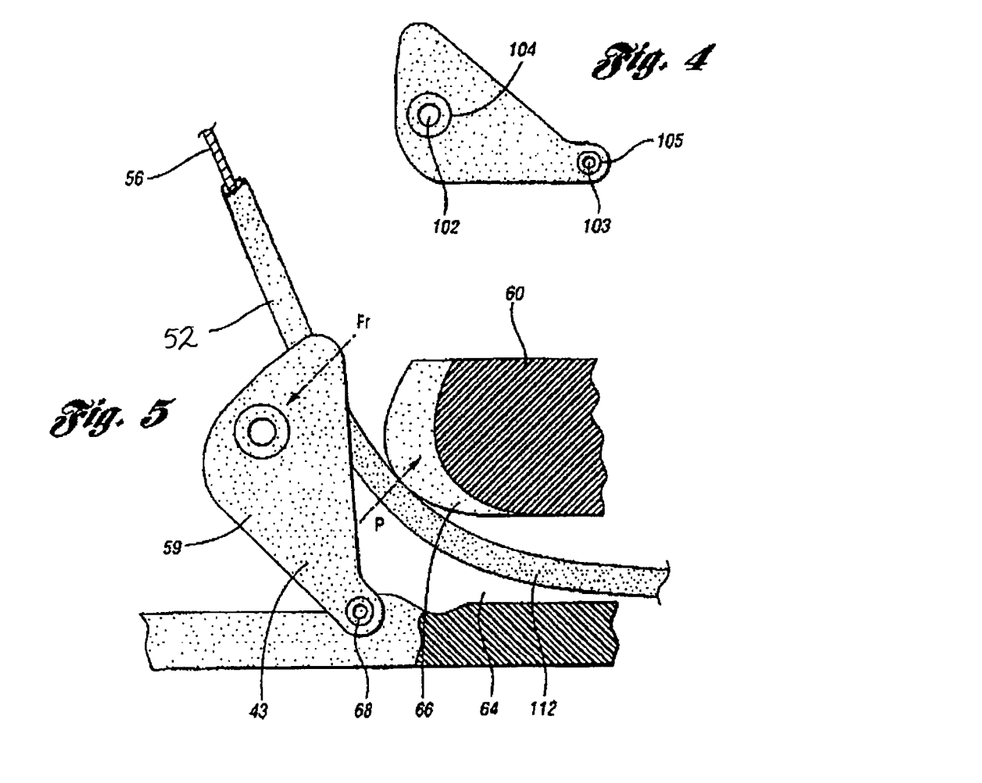
FIG. 4 is a side view of an elevator in accordance with one embodiment of the present invention.
FIG. 5 is a cross-sectional view of the tip of the endoscope of FIG. 1, depicting a wire guide secured by an elevator.

In this embodiment, the elevator 43 is moved about the elevator turning support 68 by manipulating or actuating the control system 14 to pull or retract the elevator wire 90. As shown in FIG. 5, the result moves the wire guide 56 and catheter 52 in the direction of the arrow P and pushes the elevator 43 against the cuff 60. Because the wire guide 56 is formed from a relatively axially stiff material, it tends to remain straight when pushed against the cuff 60, creating a reactive force in the direction of the arrow Fr in FIG. 5. By means of this reactive force, the wire guide 56 and catheter 52 are pressed against the slot 91. Moreover, as the elevator 43 and the cuff 60 press against one another, the wire guide and catheter are secured.

In another embodiment, FIGS. 4 and 5 illustrate the elevator 43 having a transverse passageways 102 and 103 formed therethrough, each having optional metal sleeves 104 and 105, respectively, disposed thereon. The metal sleeves are configured to provide transverse rigidity to the elevator. The proximal end of the elevator 43 is attached so as to pivot around the elevator turning support 68 provided to the cuff 60.

The elevator 43 is preferably but not necessarily comprised of polymeric material. The polymeric material may include polytetrafluoroethylene (PTFE), polyethylene, polypropylene, perfluoroelastomer, fluoroelastomer, nitrile, neoprene, polyurethane, silicone, styrene-butadiene, rubber, or polyisobutylene, or a mixture thereof. The polymeric material aids the elevator in relatively firmly grasping the medical device while reducing the risk of tearing, scraping, or striping of the medical device.

Figure 6:
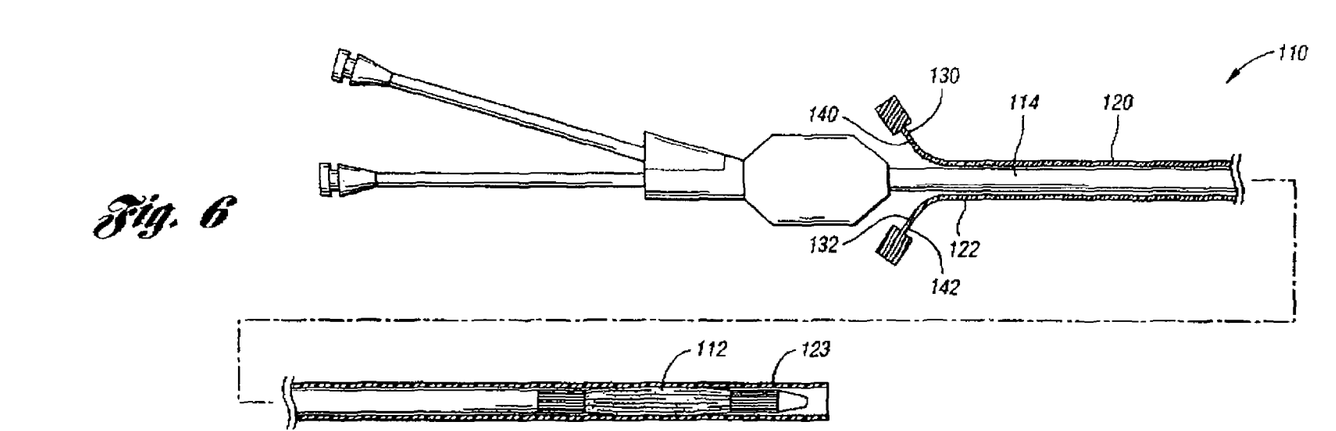
FIG. 6 is cross-sectional view of an endoscopic apparatus having a balloon disposed in a catheter in accordance with one embodiment of the present invention.
Figure 7:
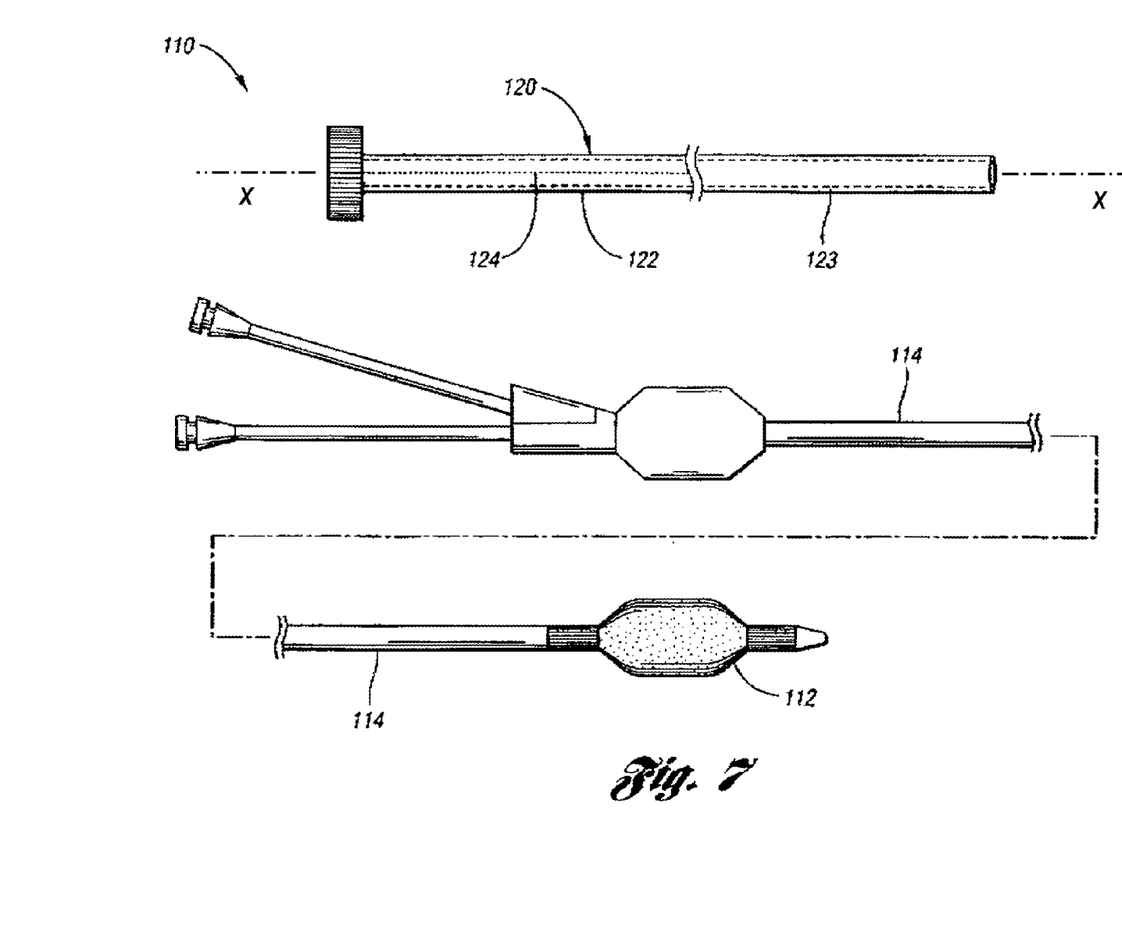
FIG. 7 is an exploded view of the endoscopic apparatus of FIG. 6.

FIGS. 6 and 7 illustrate an endoscopic apparatus 110 for treating a stricture in a body duct. As shown, the apparatus 110 comprises an inflatable or expandable balloon 112 disposable through the insertion tube 12 of the endoscope (discussed above). The apparatus 110 may be disposed through one of the working channels of the endoscope, e.g., working channel 63 mentioned above. The apparatus 110 is preferably used for dilitating a stricture in a body duct.

In this embodiment, the expandable balloon 112 is part of an inflatable balloon catheter 114. The balloon catheter 114 may be any suitable balloon catheter. In this example, the balloon catheter 114 is a biliary balloon catheter. However, the balloon catheter may be a dilatation balloon catheter, or any other suitable balloon catheter without falling beyond the scope or spirit of the present invention.

The inflatable balloon catheter 114 is preferably made any suitable material, e.g., polymeric material. For example, the inflatable balloon catheter may comprise at least one of the following components: polytetrafluoroethylene (PTFE), polyethylene, polypropylene, perfluoroelastomer, fluoroelastomer, nitrile, neoprene, polyurethane, silicone, styrene-butadiene, latex, and polyisobutylene.

Figure 8:
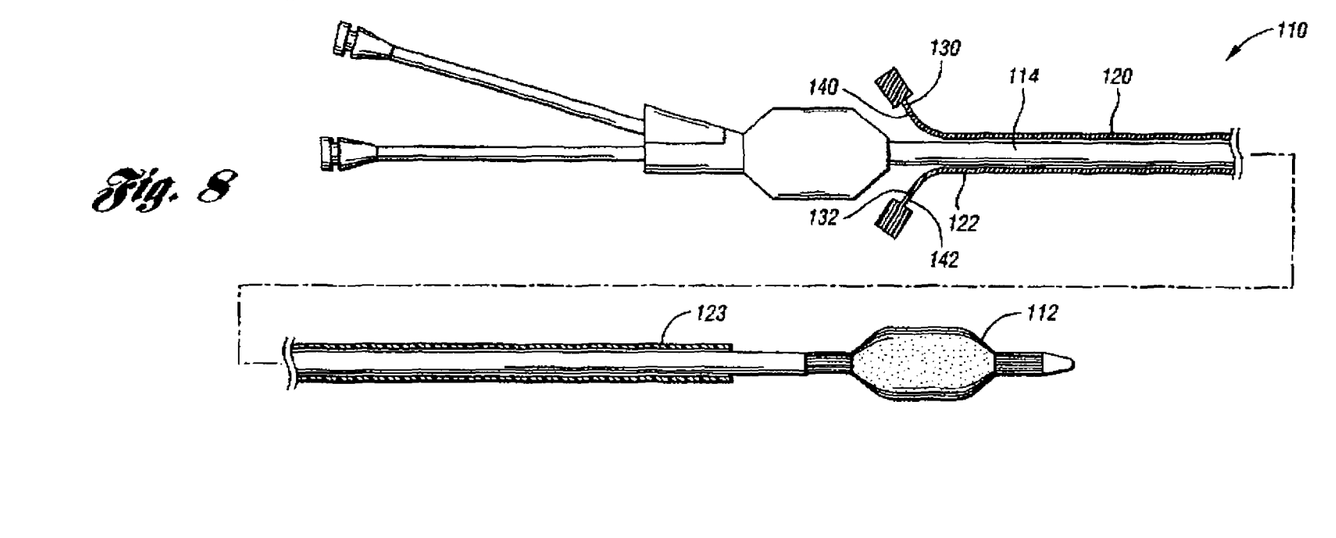
FIG. 8 is cross-sectional view of the endoscopic apparatus having the balloon deployed from the catheter.

As shown in FIGS. 6-8, the apparatus 110 further comprises an outer catheter or sheath 120. The outer catheter 120 is configured to receive the expandable balloon 112 and inflatable balloon catheter 114 and to be disposed through the insertion tube 12 of the endoscope. Thus, the outer catheter 120 is disposed over the balloon catheter 114 when introduced through the insertion tube 12 to protect the balloon catheter 114 from scraping or tearing on the elevator on the distal tip. In this embodiment, the outer catheter 120 comprises proximal and distal portions 122, 123 along a longitudinal axis X thereof. Preferably, at least the proximal portion 122 is comprised of a molecular structure that allows it to tear or split (splittable portions are shown by reference numeral 124) along the longitudinal axis X to define first and second sections 130, 132 of the proximal portion 122. For example, the outer catheter 120 may be made of PTFE to tear or split when pulled apart.

Examples of such molecular structure of at least the proximal portion may be found in U.S. Pat. No. 4,306,562 to Osborne entitled, "Tear Apart Cannula" issued on Dec. 22, 1981; U.S. Reissued Pat. No. 31,855 to Osborne entitled, "Tear Apart Cannula" issued on Mar. 26, 1985; and U.S. Pat. No. 4,581,025 to Timmermans entitled, "Sheath" issued on Apr. 8, 1986, the entire contents of each are incorporated herein by reference. For example, U.S. Pat. No. 4,306,562 discloses that the proximal end of the cannula is slit longitudinally producing two open ended slits at opposite sides of the tubular structure, thus creating two tabs which are attached to knobs by being inserted between the screw and socket portions of the knobs. The cannula may be split apart into two portions. In the manufacturing of the cannula, Teflon tubing is cut off radially to define one end of the cannula and slit at that one end with a cutting instrument at opposite sides of the same end to form the two opposed slits. This slitting operation creates tabs which are used to pull apart the cannula and the slits define the location of the beginning of the tears when the tabs are pulled. Claim 1 discloses a cannula comprising: a tubular structure having one end which has a pair of open ended slits, said tubular structure being compatible for insertion within the body and having an opposite end adapted to be inserted in the body with said one end extending out of the body, said tubular structure being formed of flexible material having the physical property of molecular orientation whereby a tear in said material runs readily only in a longitudinal direction along the length of said tubular structure, said tubular structure being flexible from its inner diameter to its outer diameter and continuously smooth on its inner surface and outer surface, said slits each having a closed end located between said one end and said opposite end; a first tab defined by said slits on one side of one end of said tubular structure; and a second tab defined by said slits on the other side of said one end of said tubular structure whereby when said tabs are pulled apart, said structure tears longitudinally along its length beginning at said closed ends and extending to the opposite end of said tubular structure.

Alternatively, at least the proximal portion is comprised of splittable or weakened portions formed along the longitudinal axis X to define the first and second sections of the proximal portion.

By way of the splittable portions 124, the first and second sections 130, 132 are able to be separate from each other at the splittable portions 124, allowing the first and second sections 130, 132 to be "peeled away" relative to the longitudinal axis X. As will be described in greater detail below, the first and second sections 130, 132 are able to be peeled away from each other to secure the outer catheter 120 in a longitudinal position relative to the balloon catheter 114 while protecting and maintaining the expandable balloon 112 at the stricture. In this embodiment, both of the proximal and distal portions 122, 123 have splittable portions 124 scored through substantially the center along the longitudinal axis X of the outer catheter 120 to define first and second halves of the catheter 140, 142.

In this embodiment, the outer catheter 120 is made of any suitable material, e.g., polymeric material. For example, the polymeric material may comprise at least one of the following components: polytetrafluoroethylene, polyethylene, polypropylene, perfluoroelastomer, fluoroelastomer, nitrile, neoprene, polyurethane, silicone, polytetrafluroethylene, styrene-butadiene, rubber, and polyisobutylene.

In one example, the present invention provides a method of treating a stricture in a body duct. In this example, the elevator and the endoscopic system mentioned above is prepared for use. Upon completion of preparing of the endoscope, the insertion tube 12 thereof is introduced preferably orally adjacent to a stricture in a body duct, e.g., of the gallbladder. The elevator of the distal tip is positioned proximally adjacent the stricture.

In this example, a wire guide is then disposed through the insertion tube for placement of devices over the wire guide, e.g., a catheter, to a diliation location in the body duct. This may be accomplished by inserting the wire guide through a channel port of the endoscope. The wire guide is worked through the insertion tube such that the wire guide is positioned past the elevator of the distal tip to a location proximal relative to the stricture.

The method further comprises introducing the outer catheter over the wire guide and through the insertion tube. This is accomplished by inserting the outer catheter through the channel port. The catheter is worked through the insertion tube over the wire guide such that the distal portion of the catheter is positioned adjacent to the elevator of the distal tip. The elevator then is manipulated to position the catheter adjacent the stricture in the body duct. The catheter is now positioned at a desired longitudinal portion for deployment of the expandable balloon. The wire guide is then removed from the apparatus.

In this example, the inflatable catheter having the expandable balloon is fed through the outer catheter. The expandable balloon is fed passed the elevator and is protected by the outer catheter. The balloon is positioned adjacent the distal portion of the catheter for deployment.

As mentioned above, in this embodiment, the outer catheter now comprises the inflatable catheter having the expandable balloon disposed therein at the distal portion of the outer catheter for delivery to the stricture for dilatation. As discussed, the outer catheter comprises proximal and distal portions along a longitudinal axis thereof. Here, the proximal portion comprises splittable portions formed along the longitudinal axis to define first and second sections separable from each other at the splittable portions. The splittable portions are formed on the outer catheter so that a clinician may relatively easily separate the first and section sections during the procedure. In this example, the splittable portions are centrally scored along the longitudinal axis of the outer catheter, defining first and second halves. As shown in FIG. 7, the proximal portion 122 may comprise the splittable portions 124 while the distal portion 123 lacks splittable portions 124; thus, the splittable portions 124 do not extend to the distal portion 123. In other words, the distal portion 123 is not splittable, in some embodiments.

The method further comprises separating the first and second portions at the proximal portion of the outer catheter to longitudinally maintain the outer catheter relative to the balloon. This may be accomplished by starting at the proximal portion of the outer catheter and "peeling" the first and second halves from each other. That is, the splittable portions are distally torn to separate the two halves at the proximal portion. To maintain the outer catheter at the desired longitudinal position, the peeling is continued until the point of peeling abuts the endoscope port through which the outer catheter is inserted into the endoscope. The outer catheter is now unable to distally move, thereby maintaining the longitudinal position thereof as the clinician holds the outer catheter to prevent proximal movement thereof. The method further comprises deploying the balloon through the outer catheter in the body duct for treatment of the stricture.

While the present invention has been described in terms of preferred embodiments, it will be understood, of course, that the invention is not limited thereto since modifications may be made to those skilled in the art, particularly in light of the foregoing teachings.

The invention claimed is:

1. An apparatus cooperable with a grasping slot of an elevator for an endoscope having a proximal end defining an endoscope port, the apparatus comprising:
    an expandable balloon disposable through the endoscope for dilating a stricture in the body duct; and
    a catheter disposable about the expandable balloon and cooperable with the grasping slot of the elevator to secure the catheter at a stricture, the catheter comprising proximal and distal portions along a longitudinal axis thereof, the proximal portion comprising a scored splittable portion formed therealong to define first and second sections separable from each other by the scored splittable portion, and the distal portion being unscored and structured not to be split for protecting and maintaining the expandable balloon at the stricture, the first and second sections configured to be peeled from each other by tearing the scored splittable portion, thereby distally moving a point of peeling from the proximal end of the catheter until the point of peeling abuts the endoscope port such that the catheter is unable to distally move, the distal portion being secured in a longitudinal position relative to the balloon and maintaining the expandable balloon at the stricture.

2. The apparatus of claim 1 wherein the distal portion comprises a distal splittable portion.

3. The apparatus of claim 1 wherein the splittable portion is comprised of polytetrafluoroethylene to define the first and second sections.

4. The apparatus of claim 1 wherein the splittable portion is comprised of a molecular structure configured to allow tearing when pulled apart to define the first and second sections.

5. The apparatus of claim 1 wherein the expandable balloon is a dilatation balloon catheter.

6. The apparatus of claim 1 wherein the expandable balloon is made of polymeric material comprising at least one of the following components: polytetrafluoroethylene, polyethylene, polypropylene, perfluoroelastomer, fluoroelastomer, nitrile, neoprene, polyurethane, silicone, polytetrafluroethylene, styrene-butadiene, rubber, and polyisobutylene.

7. The apparatus of claim 1 wherein the catheter is made of polymeric material comprising at least one of the following components: polytetrafluoroethylene, polyethylene, polypropylene, perfluoroelastomer, fluoroelastomer, nitrile, neoprene, polyurethane, silicone, polytetrafluroethylene, styrene-butadiene, rubber, and polyisobutylene.

8. An endoscopic system comprising
an insertion tube extending to a distal tip and including an elevator movably attached thereto, the elevator having an inner side formed thereon defining a grasping slot;
an expandable balloon disposable through the insertion tube for dilitating a stricture; and
a catheter through which the expandable balloon is disposed, the catheter being disposed through an endoscope port and the insertion tube, the catheter being cooperable with the grasping slot to inhibit longitudinal movement of the catheter with respect to the elevator, the catheter comprising proximal and distal portions along a longitudinal axis thereof, the proximal portion comprising a scored splittable portion formed along the longitudinal axis to define first and second sections separable from each other at the scored splittable portion, and the distal portion being unscored and structured not to be split for securing the catheter while protecting and maintaining the expandable balloon at the stricture, the first and second sections configured to be peeled from each other by tearing the scored splittable portion, thereby distally moving a point of peeling from the proximal end of the catheter until the point of peeling abuts the endoscope port such that the catheter is unable to distally move, the distal portion being secured in a longitudinal position relative to the balloon and maintaining the expandable balloon at the stricture.

9. The apparatus of claim 8 wherein the distal portion comprises splittable portions.

10. The apparatus of claim 9 wherein the splittable portions are weakened portions formed centrally along the longitudinal axis of the catheter to define the first and second sections as first and second halves, respectively.

11. The apparatus of claim 8 wherein the splittable portions are weakened portions formed centrally along the longitudinal axis of the catheter to define the first and second sections as first and second halves, respectively.

12. The apparatus of claim 8 wherein the expandable balloon is an expandable balloon catheter being one of a rapid exchange balloon catheter, an over-the-wire balloon catheter, a high-pressure balloon catheter, a fixed wire catheter, an electrophysiology ablation catheter, a multi-lumen balloon catheter, an occlusion balloon catheter, a double balloon catheter, a single balloon catheter, an intrauterine access balloon catheter, angioplasty balloon catheter, dilatation balloon catheter, a urethral dilation balloon catheter, an esophageal balloon catheter, an endoscopic stricturoplasty biliary balloon catheter, percutaneous stricturoplasty biliary balloon catheter, a disposable balloon catheters, a hysterosalpingogram (HSG) balloon catheter, and a stent delivery balloon catheter.

13. The apparatus of claim 8 wherein the expandable balloon is made of polymeric material comprising at least one of the following components: polytetrafluoroethylene, polyethylene, polypropylene, perfluoroelastomer, fluoroelastomer, nitrile, neoprene, polyurethane, silicone, polytetrafluroethylene, styrene-butadiene, rubber, and polyisobutylene.

14. The apparatus of claim 8 wherein the catheter is made of polymeric material comprising at least one of the following components: polytetrafluoroethylene, polyethylene, polypropylene, perfluoroelastomer, fluoroelastomer, nitrile, neoprene, polyurethane, silicone, polytetrafluroethylene, styrene-butadiene, rubber, and polyisobutylene.

15. An apparatus cooperable with a grasping slot of an elevator for an endoscope, the apparatus comprising:
an expandable balloon disposable through the endoscope for dilating a stricture in the body duct; and
a catheter disposable about the expandable balloon and cooperable with the grasping slot of the elevator to secure the catheter at a stricture, the catheter comprising proximal and distal portions along a longitudinal axis thereof, the proximal portion comprising a splittable portion formed therealong to define first and second sections separable from each other, thereby distally moving a point of peeling from the proximal end of the catheter until the point of peeling abuts a port on the endoscope, the distal portion of the catheter being unscored and structured not to be split and to maintain the expandable balloon at the stricture.

16. An apparatus cooperable with a grasping slot of an elevator for an endoscope having a proximal end defining an endoscope port, the apparatus comprising:
an expandable balloon disposable through the endoscope for dilitating a stricture in the body duct; and
a catheter disposable about the expandable balloon and cooperable with the grasping slot of the elevator to secure the catheter at a stricture, the catheter comprising proximal and distal portions along a longitudinal axis thereof, the proximal portion comprising two slits to define first and second sections having tabs separated from each other by the slits, the tabs of the first and second sections configured to be pulled to peel the first and second sections from each other beginning at the two slits, thereby distally moving a point of peeling from the proximal end of the catheter until the point of peeling abuts the endoscope port, the distal portion being structured not to be split for protecting and maintaining the expandable balloon at the stricture the distal portion being secured in a longitudinal position relative to the balloon and maintaining the expandable balloon at the stricture.

* * * * *